(12) United States Patent
Giannetti et al.

(10) Patent No.: US 8,403,982 B2
(45) Date of Patent: Mar. 26, 2013

(54) DEVICE FOR THE IN SITU DELIVERY OF HEART VALVES

(75) Inventors: Arnaldo Giannetti, Crescentino (IT); Laura Ghione, Turin (IT); Paolo Gaschino, Castagneto Po-Torino (IT)

(73) Assignee: Sorin Group Italia S.r.l., Milan (IT)

(*) Notice: Subject to any disclaimer, the term of this patent is extended or adjusted under 35 U.S.C. 154(b) by 210 days.

(21) Appl. No.: 12/465,262

(22) Filed: May 13, 2009

(65) Prior Publication Data

US 2010/0292782 A1 Nov. 18, 2010

(51) Int. Cl.
*A61F 2/24* (2006.01)

(52) U.S. Cl. .................................... 623/2.11

(58) Field of Classification Search ............... 623/1.11, 623/2.11, 1.24, 1.26, 1.12, 2.17, 1.23, 902; 623/23.68, 2.38, 904, 6.12; 606/194, 108, 606/192, 200, 107; 600/144, 146, 147, 433, 600/434, 149, 150, 139; 604/164.09, 164.11, 604/164.12, 165.04, 171, 165.01, 165.02
See application file for complete search history.

(56) References Cited

U.S. PATENT DOCUMENTS

| | | |
|---|---|---|
| 3,671,979 A | 6/1972 | Moulopoulos |
| 4,011,947 A | 3/1977 | Sawyer |
| 4,056,854 A | 11/1977 | Boretos et al. |
| 4,477,930 A | 10/1984 | Totten et al. |
| 4,601,706 A | 7/1986 | Aillon |
| 4,624,822 A | 11/1986 | Arru et al. |
| 4,684,364 A | 8/1987 | Sawyer et al. |
| 4,722,725 A | 2/1988 | Sawyer et al. |
| 4,732,152 A | 3/1988 | Wallsten et al. |
| 4,758,151 A | 7/1988 | Arru et al. |
| 4,777,951 A | 10/1988 | Cribier et al. |
| 4,784,644 A | 11/1988 | Sawyer et al. |
| 4,994,077 A | 2/1991 | Dobben |
| 5,057,092 A | 10/1991 | Webster, Jr. |
| 5,084,151 A | 1/1992 | Vallana et al. |

(Continued)

FOREIGN PATENT DOCUMENTS

| | | |
|---|---|---|
| DE | 19546692 C2 | 11/2002 |
| DE | 19857887 B4 | 5/2005 |

(Continued)

OTHER PUBLICATIONS

European Search Report and Search Opinion of European Patent Application No. 07115960.2, dated Jan. 24, 2008.

(Continued)

*Primary Examiner* — Elizabeth Houston
*Assistant Examiner* — Jocelin Tanner
(74) *Attorney, Agent, or Firm* — Faegre Baker Daniels LLP (57) ABSTRACT

A device for deploying a cardiac valve prosthesis includes at least one constraint member for radially constraining radially expandable annular portions of the valve. The constraint member is actuatable to release the annular formations constrained thereby and permit radial expansion of these annular formations. The constraint member has associated a first, slow-acting actuating mechanism and a second, fast-acting mechanism, adapted to produce relatively slow and fast release of the annular formations constrained thereby. The device may include a first constraint member and second constraint member in the form of telescoping sleeves. The slow-acting actuating mechanism will thus act on the outer sleeve, while the fast-acting mechanism will act on the inner sleeve to produce, respectively, slow and fast release of the annular formations.

11 Claims, 5 Drawing Sheets

US 8,403,982 B2

Page 2

U.S. PATENT DOCUMENTS

| | | | |
|---|---|---|---|
| 5,123,919 A | 6/1992 | Sauter et al. | |
| 5,133,845 A | 7/1992 | Vallana et al. | |
| 5,181,911 A | 1/1993 | Shturman | |
| 5,201,757 A | 4/1993 | Heyn et al. | |
| 5,287,848 A | 2/1994 | Cubb et al. | |
| 5,304,189 A | 4/1994 | Goldberg et al. | |
| 5,332,402 A | 7/1994 | Teitelbaum | |
| 5,370,684 A | 12/1994 | Vallana et al. | |
| 5,370,685 A | 12/1994 | Stevens | |
| 5,387,247 A | 2/1995 | Vallana et al. | |
| 5,397,351 A | 3/1995 | Pavcnik et al. | |
| 5,411,552 A | 5/1995 | Andersen et al. | |
| 5,423,886 A | 6/1995 | Arru et al. | |
| 5,433,723 A * | 7/1995 | Lindenberg et al. | 606/198 |
| 5,445,646 A | 8/1995 | Euteneuer et al. | |
| 5,545,214 A | 8/1996 | Stevens | |
| 5,554,185 A | 9/1996 | Block et al. | |
| 5,556,414 A | 9/1996 | Turi | |
| 5,662,712 A | 9/1997 | Pathak et al. | |
| 5,693,083 A | 12/1997 | Baker et al. | |
| 5,766,151 A | 6/1998 | Valley et al. | |
| 5,772,693 A | 6/1998 | Brownlee | |
| 5,782,811 A | 7/1998 | Samson et al. | |
| 5,824,064 A | 10/1998 | Taheri | |
| 5,840,081 A | 11/1998 | Andersen et al. | |
| 5,849,005 A | 12/1998 | Garrison et al. | |
| 5,855,597 A | 1/1999 | Jayaraman | |
| 5,855,601 A | 1/1999 | Bessler et al. | |
| 5,871,489 A | 2/1999 | Ovil | |
| 5,925,063 A | 7/1999 | Khosravi | |
| 5,951,600 A | 9/1999 | Lemelson | |
| 5,954,766 A | 9/1999 | Zadno Azizi et al. | |
| 5,957,949 A | 9/1999 | Leonhardt et al. | |
| 5,980,570 A | 11/1999 | Simpson | |
| 6,010,530 A | 1/2000 | Goicoechea | |
| 6,010,531 A | 1/2000 | Donlon et al. | |
| 6,029,671 A | 2/2000 | Stevens | |
| 6,030,360 A | 2/2000 | Biggs | |
| 6,090,099 A | 7/2000 | Samson et al. | |
| 6,106,497 A | 8/2000 | Wang | |
| 6,125,852 A | 10/2000 | Stevens et al. | |
| 6,139,572 A | 10/2000 | Campbell et al. | |
| 6,168,614 B1 | 1/2001 | Andersen et al. | |
| 6,251,093 B1 | 6/2001 | Valley et al. | |
| 6,299,638 B1 | 10/2001 | Sauter | |
| 6,309,382 B1 | 10/2001 | Garrison et al. | |
| 6,346,071 B1 | 2/2002 | Mussivand | |
| 6,402,780 B2 | 6/2002 | Williamson, IV et al. | |
| 6,416,474 B1 | 7/2002 | Penner et al. | |
| 6,425,916 B1 | 7/2002 | Garrison et al. | |
| 6,454,799 B1 | 9/2002 | Schreck | |
| 6,458,153 B1 | 10/2002 | Bailey et al. | |
| 6,482,228 B1 | 11/2002 | Norred | |
| 6,572,642 B2 | 6/2003 | Rinaldi et al. | |
| 6,582,462 B1 | 6/2003 | Andersen et al. | |
| 6,607,553 B1 | 8/2003 | Healy et al. | |
| 6,641,558 B1 | 11/2003 | Aboul-Hosn et al. | |
| 6,645,197 B2 | 11/2003 | Garrison et al. | |
| 6,645,220 B1 | 11/2003 | Huter et al. | |
| 6,652,578 B2 | 11/2003 | Bailey et al. | |
| 6,685,739 B2 | 2/2004 | DiMatteo et al. | |
| 6,726,648 B2 | 4/2004 | Kaplon et al. | |
| 6,726,712 B1 | 4/2004 | Raeder Devens et al. | |
| 6,730,118 B2 | 5/2004 | Spenser et al. | |
| 6,733,525 B2 | 5/2004 | Yang et al. | |
| 6,767,362 B2 | 7/2004 | Schreck | |
| 6,769,434 B2 | 8/2004 | Liddicoat et al. | |
| 6,805,711 B2 | 10/2004 | Quijano et al. | |
| 6,830,584 B1 | 12/2004 | Seguin | |
| 6,830,585 B1 | 12/2004 | Artof et al. | |
| 6,875,231 B2 | 4/2005 | Anduiza et al. | |
| 6,893,460 B2 | 5/2005 | Spenser et al. | |
| 6,908,481 B2 | 6/2005 | Cribier | |
| 6,913,618 B2 | 7/2005 | Denardo et al. | |
| 6,945,957 B2 | 9/2005 | Freyman | |
| 6,964,673 B2 | 11/2005 | Tsugita et al. | |
| 6,974,464 B2 | 12/2005 | Quijano et al. | |
| 6,981,942 B2 | 1/2006 | Khaw et al. | |
| 6,991,646 B2 | 1/2006 | Clerc et al. | |
| 7,001,423 B2 | 2/2006 | Euteneuer et al. | |
| 7,018,406 B2 | 3/2006 | Seguin et al. | |
| 7,018,408 B2 | 3/2006 | Bailey et al. | |
| 7,041,132 B2 | 5/2006 | Quijano et al. | |
| 7,044,966 B2 | 5/2006 | Svanidze et al. | |
| 7,077,801 B2 | 7/2006 | Haverich | |
| 7,101,396 B2 | 9/2006 | Artof et al. | |
| 7,144,364 B2 | 12/2006 | Barbut et al. | |
| 7,156,872 B2 | 1/2007 | Strecker | |
| 7,195,641 B2 | 3/2007 | Palmaz et al. | |
| 7,201,761 B2 | 4/2007 | Woolfson et al. | |
| 7,329,279 B2 | 2/2008 | Haug et al. | |
| 7,338,467 B2 | 3/2008 | Lutter | |
| 7,338,520 B2 | 3/2008 | Bailey et al. | |
| 7,374,571 B2 | 5/2008 | Pease et al. | |
| RE40,377 E | 6/2008 | Williamson, IV et al. | |
| 7,399,315 B2 | 7/2008 | Iobbi | |
| 7,544,206 B2 | 6/2009 | Cohn | |
| 7,556,646 B2 | 7/2009 | Yang et al. | |
| 7,591,843 B1 * | 9/2009 | Escano et al. | 623/1.11 |
| 7,618,432 B2 | 11/2009 | Pedersen et al. | |
| 7,708,775 B2 | 5/2010 | Rowe et al. | |
| 7,993,392 B2 | 8/2011 | Righini et al. | |
| 8,057,539 B2 | 11/2011 | Ghione et al. | |
| 8,070,799 B2 | 12/2011 | Righini et al. | |
| 8,114,154 B2 | 2/2012 | Righini et al. | |
| 2001/0002445 A1 | 5/2001 | Vesely | |
| 2001/0007956 A1 | 7/2001 | Letac et al. | |
| 2001/0010017 A1 | 7/2001 | Letac et al. | |
| 2001/0039450 A1 | 11/2001 | Pavcnik et al. | |
| 2001/0044591 A1 | 11/2001 | Stevens et al. | |
| 2002/0029075 A1 | 3/2002 | Leonhardt | |
| 2002/0042651 A1 | 4/2002 | Liddicoat et al. | |
| 2002/0045846 A1 | 4/2002 | Kaplon et al. | |
| 2002/0058995 A1 | 5/2002 | Stevens | |
| 2002/0099431 A1 | 7/2002 | Armstrong et al. | |
| 2002/0107531 A1 | 8/2002 | Schreck et al. | |
| 2002/0117264 A1 | 8/2002 | Rinaldi et al. | |
| 2002/0123802 A1 * | 9/2002 | Snyders | 623/2.18 |
| 2002/0138138 A1 | 9/2002 | Yang | |
| 2002/0151970 A1 | 10/2002 | Garrison et al. | |
| 2002/0198594 A1 | 12/2002 | Schreck | |
| 2003/0014104 A1 | 1/2003 | Cribier | |
| 2003/0023300 A1 | 1/2003 | Bailey et al. | |
| 2003/0023303 A1 | 1/2003 | Palmaz et al. | |
| 2003/0033000 A1 | 2/2003 | DiCaprio et al. | |
| 2003/0036795 A1 | 2/2003 | Andersen et al. | |
| 2003/0055495 A1 | 3/2003 | Pease et al. | |
| 2003/0109924 A1 | 6/2003 | Cribier | |
| 2003/0130729 A1 | 7/2003 | Paniagua et al. | |
| 2003/0153974 A1 | 8/2003 | Spenser et al. | |
| 2003/0163194 A1 | 8/2003 | Quijano et al. | |
| 2003/0191521 A1 | 10/2003 | Denardo et al. | |
| 2003/0191528 A1 | 10/2003 | Quijano et al. | |
| 2004/0034411 A1 | 2/2004 | Quijano et al. | |
| 2004/0039371 A1 | 2/2004 | Tockman et al. | |
| 2004/0039436 A1 | 2/2004 | Spenser et al. | |
| 2004/0039442 A1 | 2/2004 | St. Goar et al. | |
| 2004/0049266 A1 | 3/2004 | Anduiza et al. | |
| 2004/0055606 A1 | 3/2004 | Hendricksen et al. | |
| 2004/0078072 A1 | 4/2004 | Tu et al. | |
| 2004/0093060 A1 | 5/2004 | Seguin et al. | |
| 2004/0093063 A1 | 5/2004 | Wright et al. | |
| 2004/0106976 A1 | 6/2004 | Bailey et al. | |
| 2004/0127848 A1 | 7/2004 | Freyman | |
| 2004/0147993 A1 | 7/2004 | Westlund et al. | |
| 2004/0186563 A1 | 9/2004 | Lobbi | |
| 2004/0215333 A1 | 10/2004 | Duran et al. | |
| 2004/0236170 A1 | 11/2004 | Kim | |
| 2004/0249413 A1 | 12/2004 | Allen et al. | |
| 2005/0075584 A1 | 4/2005 | Cali | |
| 2005/0075712 A1 | 4/2005 | Biancucci et al. | |
| 2005/0075713 A1 | 4/2005 | Biancucci et al. | |
| 2005/0075717 A1 | 4/2005 | Nguyen et al. | |
| 2005/0075718 A1 | 4/2005 | Nguyen et al. | |
| 2005/0075719 A1 | 4/2005 | Bergheim | |
| 2005/0075720 A1 | 4/2005 | Nguyen et al. | |
| 2005/0075724 A1 | 4/2005 | Svanidze et al. | |

| | | |
|---|---|---|
| 2005/0075726 A1 | 4/2005 | Svanidze et al. |
| 2005/0075728 A1 | 4/2005 | Nguyen et al. |
| 2005/0075729 A1 | 4/2005 | Nguyen et al. |
| 2005/0075730 A1 | 4/2005 | Myers et al. |
| 2005/0075731 A1 | 4/2005 | Artof et al. |
| 2005/0080476 A1* | 4/2005 | Gunderson et al. .......... 623/1.11 |
| 2005/0096993 A1 | 5/2005 | Pradhan et al. |
| 2005/0104957 A1 | 5/2005 | Okamoto et al. |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug et al. |
| 2005/0137693 A1 | 6/2005 | Haug et al. |
| 2005/0137694 A1 | 6/2005 | Haug et al. |
| 2005/0137695 A1 | 6/2005 | Salahieh et al. |
| 2005/0137696 A1 | 6/2005 | Salahieh et al. |
| 2005/0137697 A1 | 6/2005 | Salahieh et al. |
| 2005/0137698 A1 | 6/2005 | Salahieh et al. |
| 2005/0137699 A1 | 6/2005 | Salahieh et al. |
| 2005/0137701 A1 | 6/2005 | Salahieh et al. |
| 2005/0137702 A1 | 6/2005 | Haug et al. |
| 2005/0143809 A1 | 6/2005 | Salahieh et al. |
| 2005/0165480 A1 | 7/2005 | Jordan et al. |
| 2005/0197695 A1 | 9/2005 | Stacchino et al. |
| 2005/0240200 A1 | 10/2005 | Bergheim |
| 2005/0251251 A1 | 11/2005 | Cribier |
| 2005/0267493 A1 | 12/2005 | Schreck et al. |
| 2006/0004436 A1 | 1/2006 | Amarant et al. |
| 2006/0004439 A1 | 1/2006 | Spenser et al. |
| 2006/0020333 A1 | 1/2006 | Lashinski et al. |
| 2006/0020334 A1 | 1/2006 | Lashinski et al. |
| 2006/0025844 A1 | 2/2006 | Majercak et al. |
| 2006/0030922 A1 | 2/2006 | Dolan |
| 2006/0063199 A1 | 3/2006 | Elgebaly et al. |
| 2006/0064054 A1 | 3/2006 | Sakakine et al. |
| 2006/0074271 A1 | 4/2006 | Cotter |
| 2006/0074484 A1 | 4/2006 | Huber |
| 2006/0085060 A1 | 4/2006 | Campbell |
| 2006/0095025 A1 | 5/2006 | Levine et al. |
| 2006/0100639 A1 | 5/2006 | Levin et al. |
| 2006/0135962 A1 | 6/2006 | Kick et al. |
| 2006/0142838 A1 | 6/2006 | Molaei et al. |
| 2006/0142848 A1 | 6/2006 | Gabbay |
| 2006/0178740 A1 | 8/2006 | Stacchino et al. |
| 2006/0195134 A1 | 8/2006 | Crittenden |
| 2006/0195184 A1 | 8/2006 | Lane et al. |
| 2006/0229659 A1 | 10/2006 | Gifford et al. |
| 2006/0241656 A1 | 10/2006 | Starksen et al. |
| 2006/0271081 A1 | 11/2006 | Realyvasquez |
| 2006/0276775 A1 | 12/2006 | Rosenberg et al. |
| 2007/0010850 A1 | 1/2007 | Balgobin et al. |
| 2007/0027534 A1 | 2/2007 | Bergheim et al. |
| 2007/0032850 A1 | 2/2007 | Ruiz et al. |
| 2007/0055357 A1 | 3/2007 | Pokorney et al. |
| 2007/0088431 A1 | 4/2007 | Bourang et al. |
| 2007/0100302 A1 | 5/2007 | Dicarlo et al. |
| 2007/0100356 A1 | 5/2007 | Lucatero et al. |
| 2007/0100440 A1 | 5/2007 | Figulla et al. |
| 2007/0112355 A1 | 5/2007 | Salahieh et al. |
| 2007/0112422 A1 | 5/2007 | Dehdashtian |
| 2007/0118207 A1 | 5/2007 | Amplatz et al. |
| 2007/0118209 A1 | 5/2007 | Strecker |
| 2007/0156225 A1* | 7/2007 | George et al. ................ 623/1.12 |
| 2007/0162100 A1 | 7/2007 | Gabbay |
| 2007/0162103 A1 | 7/2007 | Case et al. |
| 2007/0162107 A1 | 7/2007 | Haug et al. |
| 2007/0162111 A1 | 7/2007 | Fukamachi et al. |
| 2007/0162113 A1 | 7/2007 | Sharkawy et al. |
| 2007/0173861 A1 | 7/2007 | Fukamachi et al. |
| 2007/0203503 A1 | 8/2007 | Salahieh et al. |
| 2007/0203561 A1 | 8/2007 | Forster et al. |
| 2007/0203575 A1 | 8/2007 | Forster et al. |
| 2007/0219630 A1 | 9/2007 | Chu |
| 2007/0250097 A1 | 10/2007 | Weitzner et al. |
| 2007/0265702 A1 | 11/2007 | Lattouf |
| 2008/0021546 A1 | 1/2008 | Patz et al. |
| 2008/0065011 A1 | 3/2008 | Marchand et al. |
| 2008/0082165 A1 | 4/2008 | Wilson et al. |
| 2008/0097595 A1 | 4/2008 | Gabbay |
| 2008/0140189 A1 | 6/2008 | Nguyen et al. |
| 2008/0147160 A1 | 6/2008 | Ghione et al. |
| 2008/0147180 A1 | 6/2008 | Ghione et al. |
| 2008/0147181 A1 | 6/2008 | Ghione et al. |
| 2008/0147182 A1 | 6/2008 | Righini et al. |
| 2008/0147188 A1 | 6/2008 | Steinberg |
| 2008/0183097 A1 | 7/2008 | Leyde et al. |
| 2008/0208216 A1 | 8/2008 | Cerier |
| 2008/0262507 A1 | 10/2008 | Righini et al. |
| 2009/0069886 A1 | 3/2009 | Suri et al. |
| 2009/0069887 A1 | 3/2009 | Righini et al. |
| 2009/0069889 A1 | 3/2009 | Suri et al. |
| 2009/0069890 A1 | 3/2009 | Suri et al. |
| 2009/0105794 A1 | 4/2009 | Ziarno et al. |
| 2009/0118580 A1 | 5/2009 | Sun et al. |
| 2009/0157174 A1 | 6/2009 | Yoganathan et al. |
| 2009/0164004 A1 | 6/2009 | Cohn |
| 2009/0164006 A1 | 6/2009 | Seguin et al. |
| 2009/0171363 A1 | 7/2009 | Chocron |
| 2009/0171456 A1 | 7/2009 | Kveen et al. |
| 2009/0177275 A1 | 7/2009 | Case |
| 2009/0228093 A1 | 9/2009 | Taylor et al. |
| 2009/0234443 A1 | 9/2009 | Ottma et al. |
| 2009/0240326 A1 | 9/2009 | Wilson et al. |
| 2009/0254165 A1 | 10/2009 | Tabor et al. |
| 2009/0281609 A1 | 11/2009 | Benichou et al. |
| 2009/0281619 A1 | 11/2009 | Le et al. |
| 2010/0191326 A1* | 7/2010 | Alkhatib ...................... 623/2.11 |
| 2010/0292783 A1 | 11/2010 | Giannetti et al. |
| 2010/0292784 A1 | 11/2010 | Giannetti et al. |
| 2012/0053684 A1 | 3/2012 | Righini |

FOREIGN PATENT DOCUMENTS

| | | |
|---|---|---|
| EP | 133420 B1 | 2/1988 |
| EP | 0155245 B1 | 5/1990 |
| EP | 0592410 B1 | 10/1995 |
| EP | 0512359 B1 | 12/1996 |
| EP | 0515324 B1 | 12/1996 |
| EP | 0850607 A1 | 7/1998 |
| EP | 1057460 A1 | 12/2000 |
| EP | 1356763 A2 | 10/2003 |
| EP | 1356793 A2 | 10/2003 |
| EP | 0852481 B1 | 2/2004 |
| EP | 1440671 A2 | 7/2004 |
| EP | 1088529 B1 | 6/2005 |
| EP | 0955895 B1 | 8/2005 |
| EP | 1488735 B1 | 6/2007 |
| EP | 1212989 B1 | 1/2008 |
| EP | 1653884 B1 | 6/2008 |
| EP | 1935377 A1 | 6/2008 |
| EP | 1955643 A1 | 8/2008 |
| EP | 1570809 B1 | 1/2009 |
| EP | 2033581 A1 | 3/2009 |
| EP | 2033597 A1 | 3/2009 |
| FR | 2828091 A1 | 2/2003 |
| WO | WO 97/24989 A1 | 7/1997 |
| WO | WO 98/17202 A1 | 4/1998 |
| WO | WO 98/29057 A1 | 7/1998 |
| WO | WO 99/04728 A1 | 2/1999 |
| WO | WO 99/56665 A1 | 11/1999 |
| WO | WO 00/18303 A1 | 4/2000 |
| WO | WO 00/41525 A2 | 7/2000 |
| WO | WO 00/41652 A1 | 7/2000 |
| WO | WO 01/21244 A1 | 3/2001 |
| WO | WO 01/62189 A1 | 8/2001 |
| WO | WO 01/64137 A1 | 9/2001 |
| WO | WO 01/76510 A2 | 10/2001 |
| WO | WO 02/41789 A2 | 5/2002 |
| WO | WO 02/47575 A2 | 6/2002 |
| WO | WO 02/076348 A1 | 10/2002 |
| WO | WO 03/003943 A3 | 11/2003 |
| WO | WO 03/094797 A1 | 11/2003 |
| WO | WO 2004/089253 A1 | 10/2004 |
| WO | WO 2005/046525 A1 | 5/2005 |
| WO | WO 2005/065200 A2 | 7/2005 |
| WO | WO 2005/096993 A1 | 10/2005 |

| | | | |
|---|---|---|---|
| WO | WO 2005/104957 A2 | 11/2005 |
| WO | WO 2006/054107 A2 | 5/2006 |
| WO | WO 2006/063199 A2 | 6/2006 |
| WO | WO 2006/086135 A2 | 8/2006 |
| WO | WO 2006/116558 A2 | 11/2006 |
| WO | WO 2006/135551 A2 | 12/2006 |
| WO | WO 2006/138173 A2 | 12/2006 |
| WO | WO 2007/071436 A2 | 6/2007 |
| WO | WO 2007/076463 A2 | 7/2007 |
| WO | WO 2008/097589 A1 | 8/2008 |
| WO | WO 2008/125153 A1 | 10/2008 |

OTHER PUBLICATIONS

European Search Report Issued in EP 09160184 dated Oct. 22, 2009.

European Search Report issued in EP Application 08163752, dated Dec. 29, 2008.

Partial European Search Report issued in EP App No. 06126556, mailed Apr. 16, 2007, 6 pages.

European Search Report Issued in EP Application No. 09160183, dated Oct. 2, 2009, 6 pages.

European Search Report Issued in EP Application No. 09160186, dated Oct. 6, 2009, 5 pages.

European Search Report Issued in EP Application No. 07115951, dated Sep. 24, 2009, 8 pages.

Extended European Search Report issued in EP Application 06126552, dated Jun. 6, 2007, 7 pages.

Extended European Search Report issued in EP Application 06126556, dated Jul. 6, 2007, 13 pages.

Extended European Search Report Issued in EP Application 07115960, dated Jan. 24, 2008, 8 pages.

Extended European Search Report issued in EP Application 09158822, dated Sep. 9, 2009, 5 pages.

Ho, Paul C., "Percutaneous aortic valve replacement: A novel design of the delivery and deployment system", Minimally Invasive Therapy, 2008; 17:3; 190-194.

Huber, Christoph H. et al., "Direct-Access Valve Replacement: A Novel Approach for Off-Pump Valve Implantation Using Valved Stents", Journal of the American College of Cardiology, vol. 46, No. 2, 2005, pp. 366-370.

European Search Report issued in EP Application No. 08159301, mailed Dec. 30, 2008, 6 pages.

Partial European Search Report issued in EP Application No. 10155332, dated Jun. 9, 2011, 7 pages.

* cited by examiner

DEVICE FOR THE IN SITU DELIVERY OF HEART VALVES

TECHNICAL FIELD

The present invention relates to devices for the in situ delivery of heart valves. More particularly, it relates its possible application to cardiac valve prostheses (heart valve prostheses) using minimally-invasive surgical techniques or endovascular delivery techniques.

BACKGROUND

Expandable prosthetic valves typically include an expandable and collapsible anchoring structure or armature, which is able to support and fix the valve prosthesis in the implantation position, and prosthetic valve elements, generally in the form of leaflets or flaps, which are stably connected to the anchoring structure and are able to regulate blood flow.

These expandable prosthetic valves enable implantation using various minimally invasive or sutureless techniques. Exemplary applications for such an expandable valve prosthesis include aortic and pulmonary valve replacement. Various techniques are generally known for implanting an aortic valve prosthesis and include percutaneous implantation (e.g., transvascular delivery), dissection of the ascending aorta using minimally invasive thoracic access (e.g., mini-thoracotomy or mini-sternotomy), and transapical delivery wherein the aortic valve annulus is accessed through an opening near the apex of the left ventricle. The percutaneous and thoracic access approaches involve delivering the prosthesis in a direction opposing blood flow (i.e., retrograde), whereas the transapical approach involves delivering the prosthesis in the same direction as blood flow (i.e., antegrade).

SUMMARY

The present invention, according to one embodiment, is a device for deploying a cardiac valve prosthesis, including a first expandable portion and a second expandable portion, at an implantation site. The device includes a first constraint member for radially constraining the first expandable portion, a second constraint member for radially constraining the second expandable portion, a rotary actuation member coupled to the first constraint for retracting the first constraint such that the first expandable portion is deployed, and a slidable actuation member coupled to the second constraint member for retracting the second constraint such that the second expandable portion is deployed. The first and the second actuation members are independently adjustable, such that the first and second expandable portions may be independently deployed.

The present invention, according to another embodiment, is a device for deploying a cardiac valve prosthesis including radially expandable annular portions, the device including at least one constraint member for radially constraining the annular portions, the at least one constraint member actuatable to release the annular portions constrained thereby to permit radial expansion of the annular portions, wherein the at least one constraint member has associated a first, slow-acting actuating mechanism and a second, fast-acting mechanism, respectively, to produce relatively slow and fast release of the annular portions constrained thereby.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

DETAILED DESCRIPTION

In the following description, numerous specific details are given to provide a thorough understanding of embodiments. The embodiments can be practiced without one or more of the specific details, or with other methods, components, materials, etc. Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

FIGS. 1-5 show a prosthetic valve delivery device 100. The device 100 includes a handle 1 for manipulation by a practitioner and a holder unit 10 for a valve V to be delivered. As shown, the handle 1 and the holder unit 10 are generally located at proximal and distal ends of the device 100.

As used herein, "proximal" and "distal" refer to the conditions of handling of the device 100 by a practitioner who manipulates the device via the handle 1 at the "proximal" end in order to permit delivery of the valve V at the "distal" end of the device 100. Thus "proximal" and "distal," as used herein, have no direct relationship to the approach (retrograde or antegrade) adopted for delivering the valve V.

Figure 1:
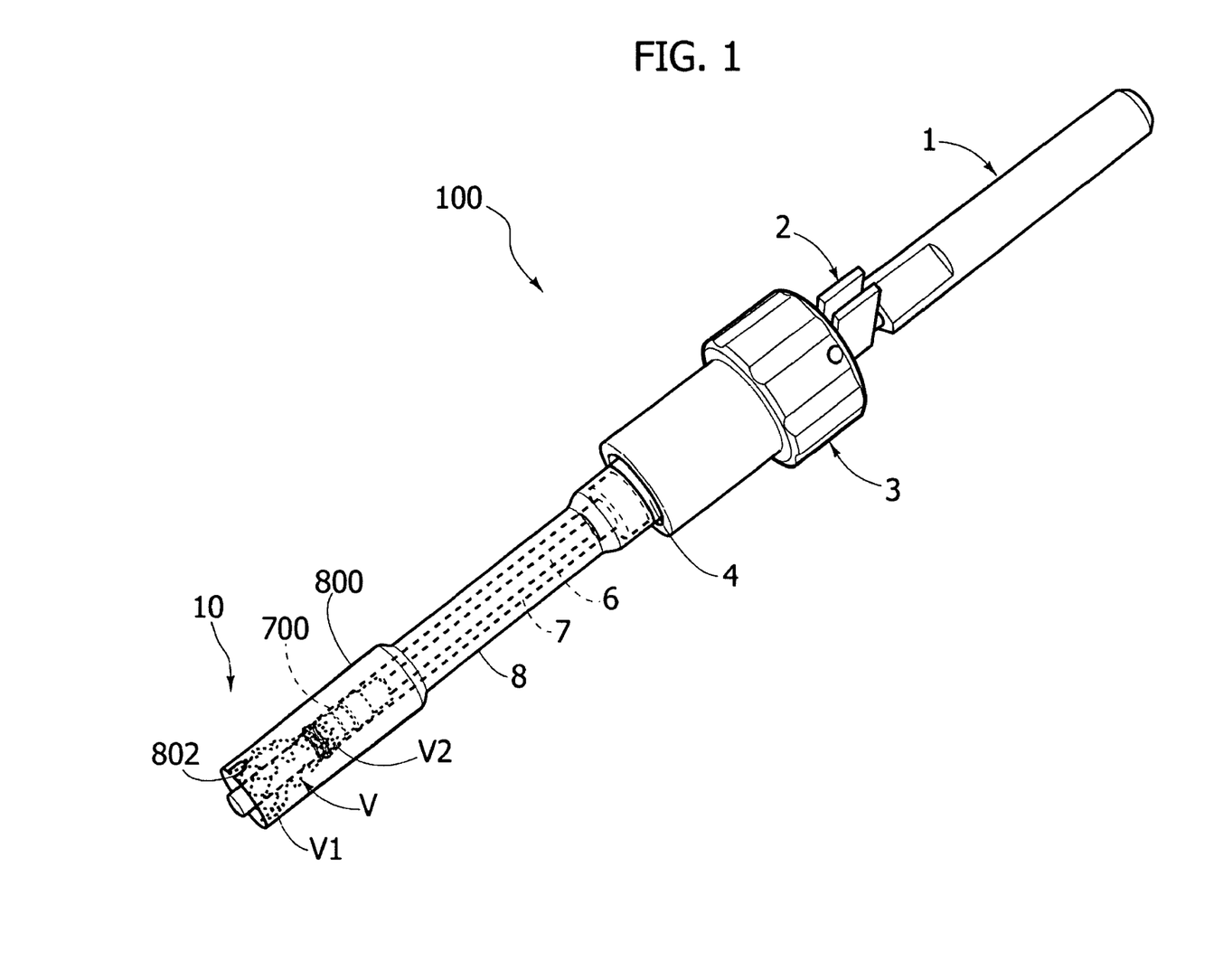
FIG. 1 is a general perspective view of a device as described herein.

In one exemplary embodiment, the valve V is of the type disclosed in U.S. Publication 2006/0178740, which is incorporated herein by reference. Such a prosthetic valve includes two annular end portions V1, V2 (i.e. inflow and outflow with respect to the direction of unimpeded flow of blood through the valve). As shown in FIG. 1, the valve is arranged in the holder unit 10 at the distal delivery end of the device 100 with the annular portions V1, V2 in a radially contracted condition.

In the exemplary illustrated arrangement, the annular portions V1 and V2 are located "distally" and "proximally," respectively of each other with reference to the orientation of the device 100. In the following it will be assumed that the valve V is delivered by releasing the annular portion V1 first and then by causing the valve V to gradually expand (e.g. due to its elastic or superelastic nature), starting from the portion V1 and continuing to the portion V2, until expansion is complete.

Figure 2:
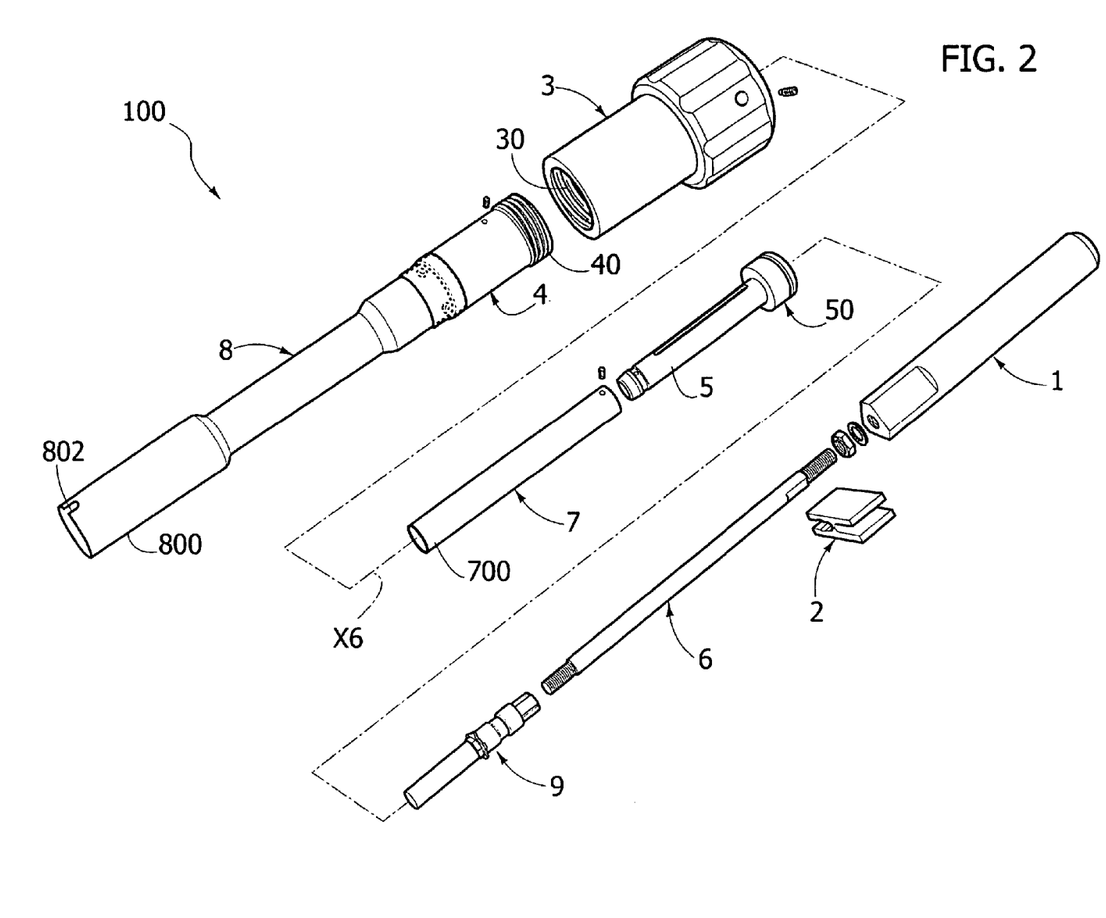
FIG. 2 is a general exploded view showing various components of the device of FIG. 1.

As shown in the exploded view of FIG. 2, a shaft 6 (which may be either rigid or flexible) extends from the handle 1 to the holder unit 10 for the valve. The holder unit includes an annular groove or similar recessed 9 formation adapted to receive the (proximal) annular portion V2 of the valve V in a radially contracted condition.

A tubular sheath or sleeve is slidably arranged over the shaft 6. Such a sleeve (hereinafter the "inner" sleeve) includes a proximal portion 5 proximate the handle 1 as well as a distal portion 7. The inner sleeve is of a length such that it can extend axially over the shaft 6 to form with its marginal end an intermediate tubular member 700 of the holder unit 10 which surrounds the formation 9 to radially constrain and retain the annular portion V2 of the valve V located therein. In various embodiments, the sleeve is of the type described in co-pending, commonly assigned U.S. patent application Ser. No. 12/465,278, filed on even date herewith, entitled "DEVICE FOR THE IN SITU DELIVERY OF HEART VALVES," which is incorporated herein by reference.

The proximal portion 5 of the inner sheet or sleeve terminates in an annular member 50 adapted to abut against a stop member 2. When in place on the shaft 6, the stop member 2 prevents the inner sleeve from being retracted (i.e. slid back) along the axis X6 of the shaft 6 from the position shown in FIG. 1, where the intermediate member or constraint 700 of the holder unit 10 radially constrains and retains the annular portion V2 of the valve V. When the stop member 2 is removed or otherwise disengaged, the inner sleeve can be retracted along the axis X6 so that the intermediate member 700 of the holder unit releases the annular portion V2 of the valve V.

In one embodiment, the stop or blocking member 2 includes a fork-shaped body (e.g. of plastics material) adapted to be arranged astride the root portion of the shaft 6 between the annular member 50 and the handle 1 to prevent "backward" movement of the inner sleeve towards the handle 1.

A further tubular sheet or sleeve (hereinafter the "outer" sleeve) is slidably arranged over the inner sleeve 5, 7. The outer sleeve 4 includes a proximal portion having an outer threaded surface 40 to cooperate with a complementary threaded formation 30 provided at the inner surface of a tubular rotary actuation member 3 arranged around the proximal portion 4 of the outer sleeves. In an embodiment, the actuation member 3 encloses the annular member 50 of the inner sleeve.

The outer sleeve extends over the inner sleeve and terminates with a distal portion 8 including an terminal constraint or outer member 800 adapted to extend around the distal portion to form an external tubular member of the holder unit 10 adapted to radially constrain and retain the annular portion V1 of the valve V located therein.

According to various embodiments, the threaded surface/formations 30, 40 comprise a "micrometric" device actuatable by rotating the actuation member 3 to produce and precisely control axial displacement of the outer sleeve along the axis X6 of the shaft 6. Such a controlled movement may take place along the axis X6 of the shaft 6 starting from an extended position, as shown in FIG. 1, where the outer member 800 of the holder unit 10 radially constrains and retains the valve V In these embodiments, which allow such a gradual movement or retraction, the outer member 800 gradually releases first the annular portion V1 of the valve V and then the remaining portions of the valve located between the annular portion V1 and the annular portion V2, thus permitting gradual radial expansion of the valve V.

In one embodiment, the retraction movement produced by the "micrometric" actuation device 30, 40 actuated via the rotary member 3 is stopped when the distal marginal end of the outer member 800 is aligned with the marginal end of the intermediate member 700 which still radially constrains and retains the annular portion V2 of the valve V in the formation 9.

As further described below, in that condition, the valve V is partly expanded (i.e., more or less "basket-like") with the annular portion V1 completely (or almost completely) expanded and the annular portion V1 still contracted.

Starting from that position, if the stop member 2 is removed or otherwise disengaged, both the inner sleeve and the (retracted) outer sleeve mounted thereon can be slid back along the axis X6 towards the handle 1. In that way, the intermediate member 700 of the holder unit releases the annular portion V2 of the valve V thus permitting valve expansion to become complete. Valve expansion is not hindered by the member 800 as this is likewise retracted towards the handle 1.

FIG. 1 depicts the device 100 where the device has a valve V mounted in the holder portion 10 for delivery into a patient's body (e.g., via a minimally-invasive or percutaneous procedure). Many such procedures are well known in the art.

In the condition shown in FIG. 1, the inner and outer sleeves are axially located over the shaft 6 in a telescoped arrangement in such a way that: the intermediate member 700 of the holder portion 10 (i.e., the distal end of the inner sleeve 5, 7) surrounds and radially constrains the annular portion V2 of the valve V in the annular formation 9, and the outer member 800 of the holder portion 10 (i.e. the distal end of the outer sleeve 4, 8) surrounds and radially constrains the annular portion V1 of the valve V.

Figure 3:
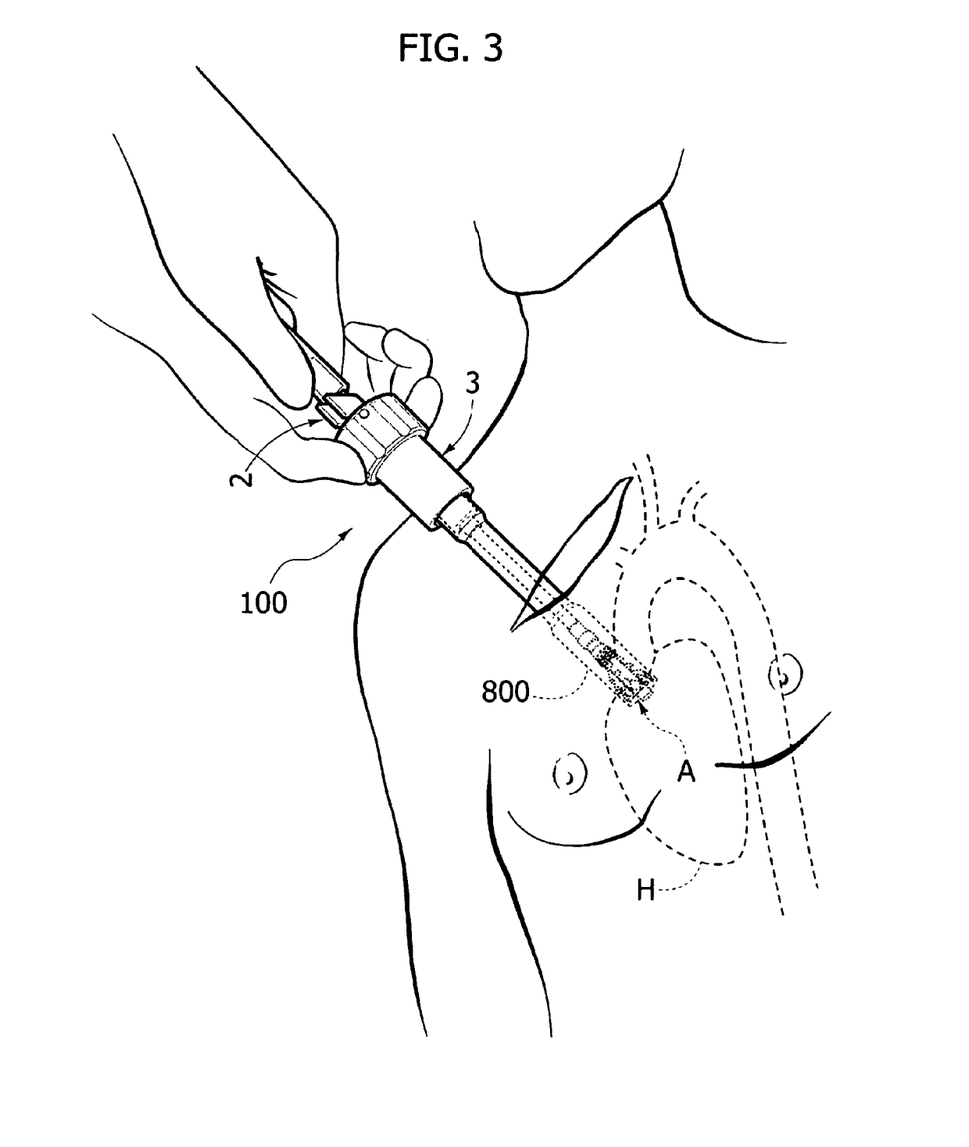
FIGS. 3 to 5 show exemplary techniques of delivering a heart valve by using the device of FIGS. 1 and 2.

In an exemplary delivery procedure of the valve V, the practitioner introduces the device 100 into the patient's body and advances it through the delivery route or path until the outer member 800 is located at the annulus of the natural valve to be substituted by the valve V (see, e.g., FIG. 3, where H generally denotes the patient's heart). The practitioner may use any of a variety of known techniques for delivering the device 100 to the valve annulus site. In the exemplary case considered here, the valve to be replaced is the aortic valve.

In various embodiments, the radial dimensions of outer member 800 are slightly less than the radial dimensions of the annulus of the natural valve intended to be substituted. In these embodiments, the outer member 800 will not unduly move about or "dance," while being positioned within the natural annulus. In various exemplary embodiments, these radial dimensions are in the range of between about 10 mm and about 27 mm.

In the exemplary case of aortic valve replacement, this may involve the outer member 800 being located immediately distally (with respect to the flow direction blood pumped from the left heart ventricle) of the aortic annulus so that the annular portions V1 and V2 are located on opposite sides (i.e. astride) of the Valsalva sinuses. In other words, the portion V1 is located on one of the ventricle side and the aortic root side of the Valsalva sinuses, and the portion V2 is located on the opposite side of the Valsalva sinuses.

Once the portion 800 is disposed properly at the annulus site, the practitioner will actuate the rotary actuation member 30 by rotating it in such a way that cooperation of the threaded sections 30 and 40 will cause the outer sleeve 4, 8 to start gradually retracting towards the handle 1. As a result of this retraction of the outer sleeve, the outer member 800 will gradually disengage the annular portion V1 of the valve V. The annular portion V1 will thus be allowed to radially expand as schematically shown in FIG. 3. The exemplary aortic replacement procedure shown in FIGS. 3 to 5 employs a retrograde approach such that the annular portion V1 will be the inflow side of the valve V. As discussed above, however, according to various embodiments, the delivery approach is either retrograde or antegrade and the portion V1 is either of the inflow or the outflow portion.

Figure 4:
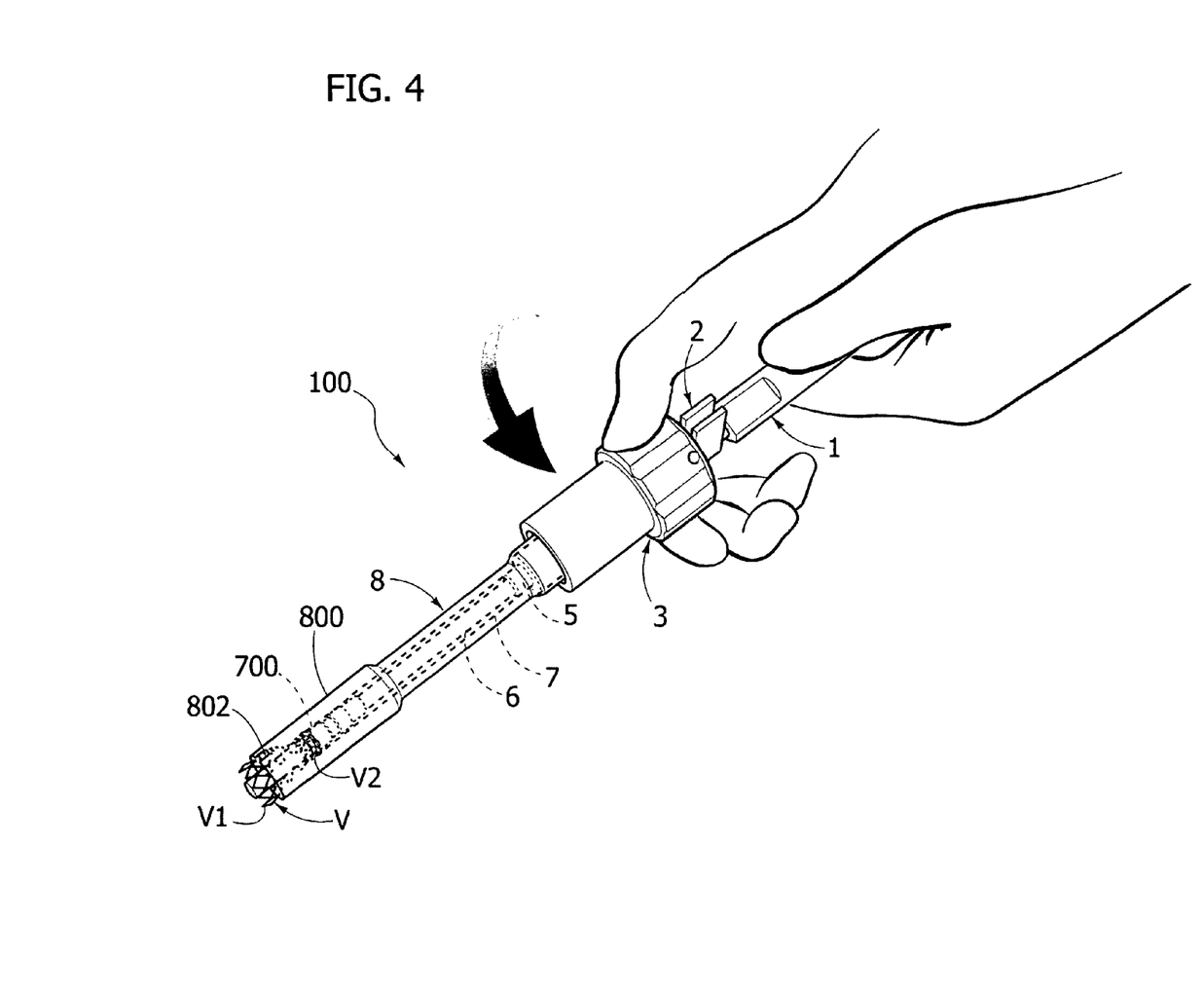

Gradual withdrawal of the outer sleeve 4, 8 proceeds as schematically shown in FIG. 4 until the outer member 800 has almost completely disengaged the valve V, while the annular formation V2 is still securely retained by the intermediate member 700 of the inner sleeve 5, 7 which maintains the annular formation V2 of the valve on the holder portion 9. This deployment mechanism of the annular formation V1 and the valve V may be controlled very precisely by the practitioner via the screw-like mechanism 30, 40 actuated by the rotary member 3. Deployment may take place in a gradual and easily controllable manner by enabling the practitioner to verify how deployment takes place.

Also, so long as the annular formation V2 of the valve V is still constrained within the formation 9 by the intermediate member 700, the practitioner still retains firm control of the partial (e.g., "basket-like") expanded valve V. The practitioner will thus be able to adjust the position of the valve V both axially and radially (e.g., by rotating the valve V around its longitudinal axis). This radial adjustment allows the practitioner to ensure that radially expanding anchoring formations of the valve V are properly aligned with the Valsalva sinuses to firmly and reliably retain in place the valve V once finally delivered.

Figure 5:
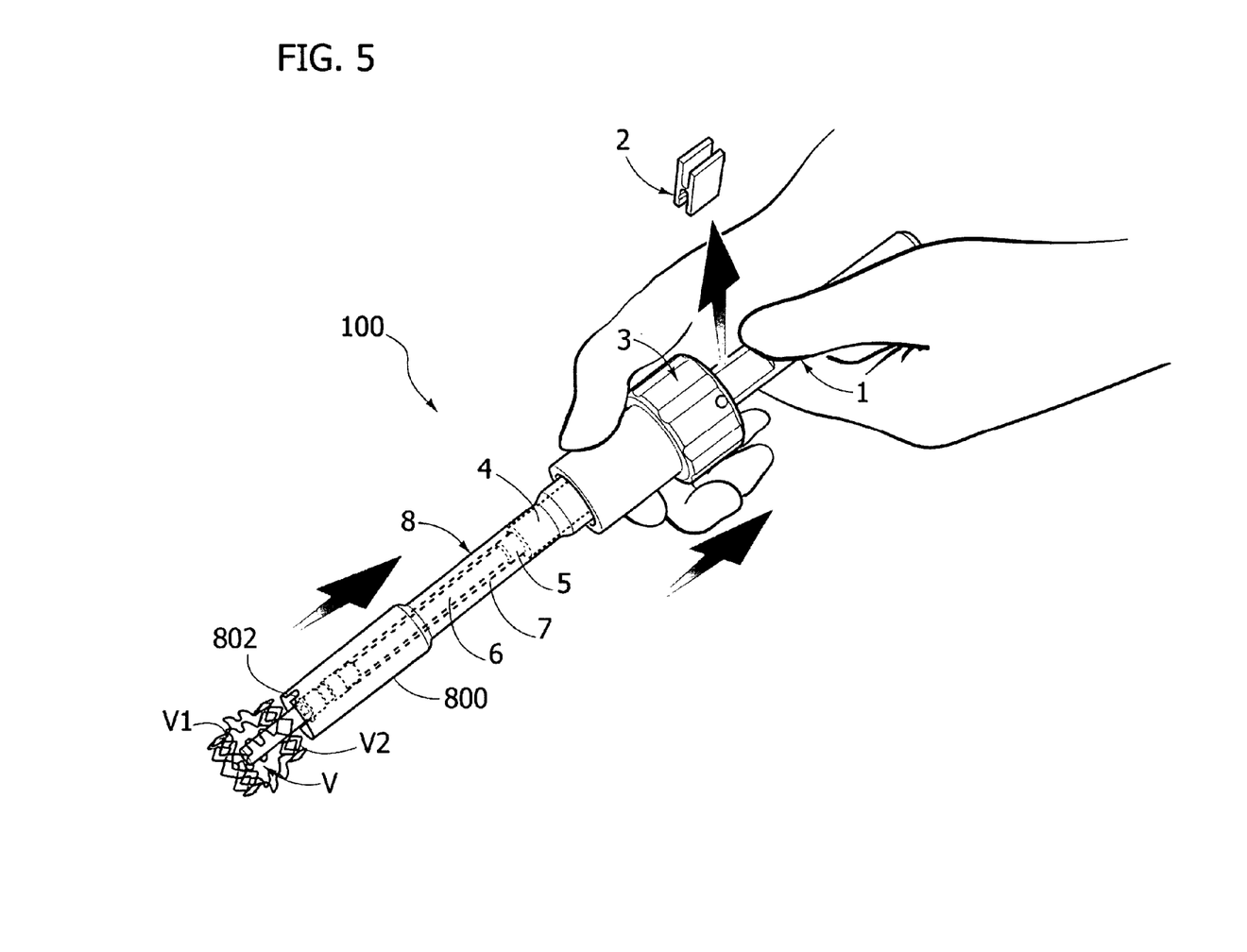

With the valve V retained by the device 100 almost exclusively via the intermediate member 700 acting on the annular formation V2, the blocking member 2 can be removed from the shaft 6 (see FIG. 5) thus permitting the inner sleeve 5, 7 (and, if not already effected previously, the outer sleeve 4,8) to be retracted in such a way to disengage the annular portion V2 of the valve as schematically shown in FIG. 5. This movement allows the annular formation V2 (and the valve V as a whole) to become disengaged from the device 100 and thus becoming completely deployed at the implantation site. This movement can be effected by sliding the inner sleeve (and the outer sleeve) towards the handle 1.

This final step of delivery of the valve V at the implantation site can be effected rapidly. This ensures that the valve V is delivered and retained by the patient's body at the position selected by the practitioner, by avoiding any undesired displacement as might arise if the final release of the valve V (i.e., release of the annular formation V1) were to take place in the same gradual, relatively slow manner as is the case for the annular formation V2.

In brief, the action described is possible because the device 100 includes a first, slow-acting actuating mechanism and a second fast-acting mechanism. The first mechanism includes the threaded portions 30, 40, actuated by the rotary member 3, which allows the annular portion V1 (and the part of the valve V between the annular portions V1 and V2) to be gradually released from the radial constraint action exerted by the member 800. The second, fast-acting mechanism, including the stop or blocking member 2 in combination with the inner sleeve 5, 7. Once the stop 2 is removed (or otherwise disabled), the inner sleeve 5, 7 (and thus the intermediate member 700 of the holder portion 10) are freely movable to release the annular formation V2 constrained thereby, thus enabling a fast release of the annular portion V2 from the radial constraint action exerted by the member 700 to complete deployment of the valve V.

In one embodiment, the portion 800 has a marginal outer edge includes one or more notches 802 to provide a reference in the angular positioning of the valve V in the annulus A.

Various embodiment do no includes the inner sleeve or at least the distal portion 7 thereof, which in various exemplary embodiments constitutes the intermediate member 700 of the holder unit 10. In these embodiments, both the annular portions V1 and V2 will be initially radially constrained by the outer member 800. In such embodiments, the first, slow-acting actuating mechanism, including the threaded portions 30, 40 actuated by the rotary member 3, will be used to withdraw the (outer) sleeve 4, 8 over the shaft 6 in order to permit the annular portion V1 (and the part of the valve V between the annular portions V1 and V2) to be gradually released.

It will be appreciated that the retraction of the sleeve 4, 8 over the shaft 6 will not lead to any axial displacement of the valve V with respect to shaft since the annular portion V2 of the valve V is received in (or otherwise engaged by) the formation 9 and thus blocked against any such axial movement.

The retraction movement of the sleeve 4, 8 over the shaft 6 will be continued under the control of the slow-acting screw mechanism 30, 40 actuated by the rotary member 3 until the marginal edge of the member 800 is located at the annular portion V2.

At that point, the second, fast-acting mechanism, including the stop or blocking member 2 will come into play. Once this member 2 is removed (or otherwise disabled), the sleeve 4, 8 (and thus the member 800 of the holder portion 10) will become freely movable (e.g., towards the handle 1) to release the annular formation V2 constrained thereby. Again, this will enable a fast release of the annular portion V2 from the radial constraint action exerted by the member 800 to complete deployment of the valve V.

In these embodiments, the radial dimensions of portion 800 are slightly less than the radial dimensions of the annulus of the natural valve intended to be substituted. In these embodiments, the outer member 800 will not unduly move about or "dance," while being positioned within the natural annulus.

It will be appreciated that while a cardiac valve prosthesis including two self-expandable annular portions has been considered herein for exemplary purposes, this disclosure may identically apply to cardiac valve prostheses including further expandable annular portions and/or one or more annular portions that are expandable via an expansion means such as an inflatable balloon.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the above described features.

We claim:

1. A device for deploying a cardiac valve prosthesis, including a first expandable portion and a second expandable portion, at an implantation site, the device comprising:
   a first constraint member for radially constraining the first expandable portion, the first constraint member comprising an outer telescoping sleeve including a proximal portion having an outer threaded surface;
   a second constraint member for radially constraining the second expandable portion, the second constraint member comprising an inner telescoping sleeve having a distal end disposed within the first constraint member and a proximal end terminating in an annular member;
   a rotary actuation member coupled to the first constraint and having a thread formation for cooperating with the outer threaded surface of the first constraint member adapted for retracting the first constraint member, such that the first expandable portion is deployed;
   a slidable actuation member coupled to the second constraint member and coupled to the first constraint member for retracting both the first and second constraint members, such that the second expandable portion is deployed; and a stop member that is removable or disengageable, wherein the annular member of the inner telescoping sleeve is adapted to abut against the stop member when the stop member is in place and to prevent the inner telescoping sleeve from being retracted;

wherein the rotary and the slidable actuation members are independently adjustable, such that the first and second expandable portions may be independently deployed,.

and wherein the first and second constraint members having associated a first slow-acting actuating mechanism and a second, fast-acting actuating mechanism, respectively, to produce relatively slow and fast release of the first and second expandable portions of the prosthesis constrained thereby.

2. The device of claim 1, wherein the second constraint member includes at least one sleeve slidably actuatable along an axis whereby the second constraint member releases the second expandable portion.

3. The device of claim 2, wherein the inner and outer telescoping sleeves are slidably actuatable along a common axis whereby the constraint members release the expandable portions constrained thereby.

4. The device of claim 1, wherein the inner and outer telescoping sleeves are configured to slide along a common axis in correspondence with one another.

5. The device of claim 1, wherein the rotary actuation member is a screw-actuated mechanism.

6. The device of claim 5, wherein the screw-actuated mechanism includes a rotary member rotatable around the outer threaded surface of the outer telescoping sleeve.

7. The device of claim 1, wherein the slidable actuation member includes a lock member which, once defeated, renders the second constraint member freely movable to release the expandable portion constrained thereby.

8. The device of claim 1, wherein the outer telescoping sleeve has a diameter of between about 10 and about 27 mm.

9. The device of claim 1, wherein the second constraint member has a marginal outer edge with at least one notch to provide a reference in the angular positioning of the cardiac valve prosthesis.

10. The device of claim 1, wherein the outer telescoping sleeve having associated the first, slow-acting actuating mechanism and the inner telescoping sleeve having associated the second, fast-acting actuating mechanism.

11. The device of claim 1, wherein when the stop member is removed or disengaged, both the inner telescoping sleeve and the outer telescoping sleeve can be retracted.

* * * * *